US012673208B2

(12) United States Patent
Cornish et al.

(10) Patent No.: US 12,673,208 B2
(45) Date of Patent: Jul. 7, 2026

(54) SYSTEM AND METHOD FOR TREATING CHRONIC PAIN

(71) Applicant: SPECIALISED PAIN MEDICINE PTY LTD, Hawthorn (AU)

(72) Inventors: Philip Cornish, Hawthorn (AU); Anne Cornish, Hawthorn (AU)

(73) Assignee: SPECIALISED PAIN MEDICINE PTY LTD, Hawthorn (AU)

( * ) Notice: Subject to any disclaimer, the term of this patent is extended or adjusted under 35 U.S.C. 154(b) by 403 days.

(21) Appl. No.: 18/257,873

(22) PCT Filed: Dec. 18, 2020

(86) PCT No.: PCT/AU2020/000142
§ 371 (c)(1),
(2) Date: Jun. 15, 2023

(87) PCT Pub. No.: WO2022/126172
PCT Pub. Date: Jun. 23, 2022

(65) Prior Publication Data
US 2024/0100338 A1 Mar. 28, 2024

(51) Int. Cl.
*A61N 1/36* (2006.01)
*A61N 1/372* (2006.01)
(52) U.S. Cl.
CPC ..... *A61N 1/36071* (2013.01); *A61N 1/36175* (2013.01); *A61N 1/37247* (2013.01)
(58) Field of Classification Search
CPC ........... A61N 1/36071; A61N 1/36175; A61N 1/37247; A61N 1/0551; A61N 1/36171;
(Continued)

(56) References Cited

U.S. PATENT DOCUMENTS 3,405,715 A * 10/1968 Hagfors ............... A61N 1/3752
607/44
2002/0065481 A1 * 5/2002 Cory .................. A61N 1/36021
604/21
(Continued)

FOREIGN PATENT DOCUMENTS

WO 2013134479 A1 12/2013

OTHER PUBLICATIONS

International Search Report for International Application No. PCT/AU2020/000142 dated Feb. 12, 2021 (5 pages).
(Continued)

*Primary Examiner* — Eugene T Wu
(74) *Attorney, Agent, or Firm* — FINNEGAN, HENDERSON, FARABOW, GARRETT & DUNNER LLP

(57) ABSTRACT

Embodiments of a method for treating a patient suffering from chronic pain are described. A source location of chronic pain in a patient is first identified. A regional anaesthetic is then used to temporarily block selected nerves to confirm the source location and identify a target nerve. An electrode array of a neuromodulation apparatus is then implanted in the patient over the target nerve, such as just under the stratum corneum, and the neuromodulation apparatus is then used to stimulate the electrode array to create a long term conduction block that provides persistent pain relief to the patient.

16 Claims, 7 Drawing Sheets

100

110 — selecting one or more nerves associated with a hypothesised source location of pain in a patient wherein each selected nerve is either
within the hypothesised source location,
in a sensory signal pathway upstream of the hypothesised source location, or
in a sensory signal pathway bounding the hypothesised source location 120 — temporarily blocking each of the selected one or more nerves using a regional anaesthetic to identify one or more target nerves 130 — implanting in the patient, an electrode array of a neuromodulation apparatus in the skin or adjacent the hypodermis to overlie at least one of the one or more target nerves, and in use, the electrode array is stimulated by the neuromodulation apparatus to provide pain relief to the patient

(58) Field of Classification Search
CPC .............. A61N 1/36128; A61N 1/0502; A61N
1/0504; A61N 1/37235; A61B 5/4824;
A61M 19/00; A61M 2202/0241; A61M
2202/048
See application file for complete search history.

(56) References Cited

U.S. PATENT DOCUMENTS

| | | |
|---|---|---|
| 2013/0190838 A1 | 7/2013 | Caparso |
| 2013/0304151 A1 | 11/2013 | Goodman et al. |
| 2019/0282267 A1 | 9/2019 | Caldwell et al. |
| 2020/0197653 A1 | 6/2020 | Boezaart et al. |

OTHER PUBLICATIONS

Cornish, P.B. et al., On the Origin of Pain-the 'Pain Channel'
Hypothesis', Medical Hypotheses, Jan. 2020, vol. 137, pp. 1-9.

* cited by examiner

100

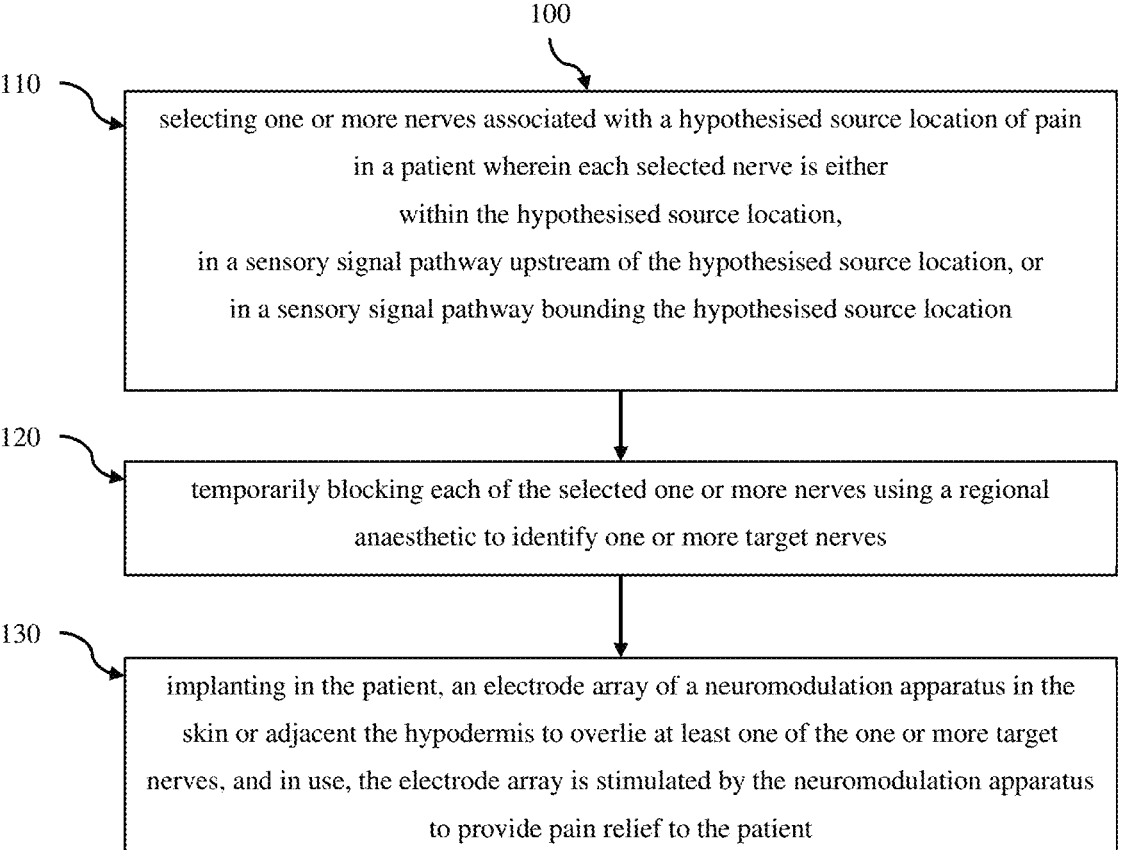

110 selecting one or more nerves associated with a hypothesised source location of pain in a patient wherein each selected nerve is either within the hypothesised source location, in a sensory signal pathway upstream of the hypothesised source location, or in a sensory signal pathway bounding the hypothesised source location

120 temporarily blocking each of the selected one or more nerves using a regional anaesthetic to identify one or more target nerves

130 implanting in the patient, an electrode array of a neuromodulation apparatus in the skin or adjacent the hypodermis to overlie at least one of the one or more target nerves, and in use, the electrode array is stimulated by the neuromodulation apparatus to provide pain relief to the patient

Figure 1

SYSTEM AND METHOD FOR TREATING CHRONIC PAIN

CROSS REFERENCE TO RELATED APPLICATION

This application is a U.S. national phase entry under 35 U.S.C. § 371 from international Application No. PCT/AU2020/000142, filed Dec. 18, 2020, the entirety of the subject matter of which is incorporated herein by reference.

TECHNICAL FIELD

The present disclosure relates to pain management. In a particular form the present disclosure relates to treatment systems for managing chronic pain in a patient.

BACKGROUND

Chronic pain is pain that lasts over an extended period of time—typically much longer than a normal injury recovery time frame. Chronic pain is frequently persistent pain that requires ongoing management to allow patients to live a normal (or as close to normal) life. It may arise due to a wide range of causes and may present as lower back pain, vertebral crush fracture, thoracic back pain, whiplash syndrome, cervicogenic headache, chronic post-surgical pain, facial pain, radicular pain, neuroma pain, phantom limb pain, pelvic pain, visceral pain and cancer survivor pain. The severity and frequency is highly variable.

Theories of pain date back to ancient times and share an understanding that pain is a phenomenon of the brain. These theories propose that stimulation (triggering) of a sensory nerve cell (nociceptor) generates a signal that travels along a nerve fibre to the spinal cord where it is transported to the brain and the signal is interpreted as a pain. One of the dominant theories for understanding pain is the gate control theory of Melzack and Wall (R. Melzack and P. D Wall, "Pain mechanisms: a new theory", Science, 150 (1965), pp. 971-978). Melzack and Wall proposed that both thin (pain) and large diameter (touch, pressure, vibration) nerve fibres carry information from the site of injury to two destinations in the dorsal horn of the spinal cord, namely transmission cells that carry the pain signal up to the brain, and inhibitory interneurons that impede transmission cell activity. Activity in thin diameter fibres excites transmission cells. Thin fibre activity impedes the inhibitory cells (tending to allow the transmission cell to fire) and large diameter fibre activity excites the inhibitory cells (tending to inhibit transmission cell activity). So, the more large fibre (touch, pressure, vibration) activity relative to thin fibre activity at the inhibitory cell, the less pain is felt. The theory offered a physiological explanation for the previously observed effect of psychology on pain perception.

In more recent times the contributions of psychological and emotional factors to the pain experience have been emphasised, becoming key factors in the development of the biopsychosocial approach for managing persistent pain. Due to the long term and persistent nature of chronic pain, many patients suffer from psychological conditions such as depression and anxiety, and may withdraw from everyday activities to avoid triggering pain.

Treatment of chronic pain may thus comprise therapeutics such as pain relievers including opioid and nonsteroidal anti-inflammatory drugs (NSAID), anticonvulsants, muscle relaxants, and anti-depressants. However many of these are only partially effective, or have unwanted side effects. For example most opioid pain relievers are addictive and their use has been linked to an increase in hospitalisations and deaths (the opioid epidemic).

Chronic pain may also be treated using medical procedures including transcutaneous electrical nerve stimulators (TENS), implantable neuromodulation units such as spinal cord stimulators, nerve blocks, and surgery. A neuromodulation unit comprises a battery and controller, and connected wires which are sheathed by a protective covering to form a lead, with each wire attached to its own electrode in an array at the end of the lead. The predominant use of neuromodulation for analgesia, known as dorsal column stimulation, has the electrode array placed in the epidural space and was pioneered by the neurosurgeon Dr Norman Shealy and his colleagues in the 1960's. More recently the electrode array has been placed in the subcutaneous tissues 'within the area of pain', a technique known as peripheral nerve field stimulation. The mechanism of action for both of these techniques is more often explained by reference to the 'gate control' theory of Melzack and Wall. In this scenario electric current from the neuromodulation unit stimulates large non-nociceptive sensory fibres, which subsequently inhibit small nociceptive fibres through interconnections within the substantia gelatinosa of the dorsal horn of the spinal cord and thereby modulate the afferent nociceptive signal to the brain. That is the neuromodulation signals disrupt the pain signals traveling between the spinal cord and the brain. However a problem with these neuromodulation devices is that they only reduce the pain and rarely eliminate the pain.

However as many of these therapeutic and surgical treatments are only partially effective or have significant side effects, additional lifestyle remedies may be prescribed such as physical therapy, psychotherapy, massage, and meditation, which often aim to enable the patient to cope with the ongoing nature of chronic pain.

There is thus a need to provide improved systems and methods for treating chronic pain, or to at least provide a useful alternative to existing systems and methods.

SUMMARY

According to a first aspect, there is provided a method for treating a patient in need of pain relief comprising:

selecting one or more nerves associated with a hypothesised source location of pain in a patient wherein each selected nerve is either within the hypothesised source location, in a sensory signal pathway upstream of the hypothesised source location, or in a sensory signal pathway bounding the hypothesised source location;

temporarily blocking each of the selected one or more nerves using a regional anaesthetic to identify one or more target nerves;

implanting in the patient, an electrode array of a neuromodulation apparatus in the skin or adjacent the hypodermis to overlie at least one of the one or more target nerves, and in use, the electrode array is stimulated by the neuromodulation apparatus to provide pain relief to the patient.

In one form, the depth of the electrode array may be selected to provide a stable field on the target nerve. In one form, the electrode array may be implanted under the stratum corneum and in the dermis or hypodermis. In a further form the electrode array may be implanted in the hypodermis and preferably such that the electrode array is adjacent the dermis in the hypodermis (i.e. in the vicinity of the boundary between the dermis and hypodermis).

Each selected nerve may be temporarily blocked for a time period sufficient to assess if blocking the nerve reduces the patient's pain below a predefined threshold level, and the target nerve is selected based on observed pain relief. Preferably the time period is sufficient to assess if blocking the nerve eliminates the patient's pain. In a further form at least one selected nerve is blocked for a time period of at least 20 hours.

In one form, the method may further comprise programming the neuromodulation apparatus to provide a continuous conduction block to the respective target nerve to provide continuous pain relief to the patient.

The method may further comprise determining the hypothesised source location of pain in the patient, through taking or reviewing a patient history, and performing a physical examination of the patient.

According to a second aspect, there is provided a neuromodulation apparatus comprising:

an implantable control unit comprising at least a control circuit, a stimulator circuit and a power supply;

at least one electrode array electrically connected to the implantable control unit, wherein in use, the electrode array is implanted over a target nerve in the patient identified by using a regional anaesthetic to block a target nerve, and the controller is configured to stimulate the electrode array to provide pain relief to the patient.

In one form, the apparatus is configured to store a pulse frequency, a pulse width, and an amplitude, and in use the pulses generated by the stimulator circuit stimulates the electrode array to provide pain relief to the patient.

In one form, the neuromodulation apparatus further comprises:

an external programming device configured to communicate with the implantable neuromodulation device, and in use is configured to allow a user to set at least a pulse frequency, a pulse width, and an amplitude of the of the stimulator circuit of the implantable neuromodulation device in order to provide pain relief to the patient.

The neuromodulation apparatus may be used in the method of the first aspect.

BRIEF DESCRIPTION OF DRAWINGS

Embodiments of the present disclosure will be discussed with reference to the accompanying drawings wherein:

FIG. 1 is a flowchart of a method for treating a patient in need of pain relief according to an embodiment;

4

Figure 2A:
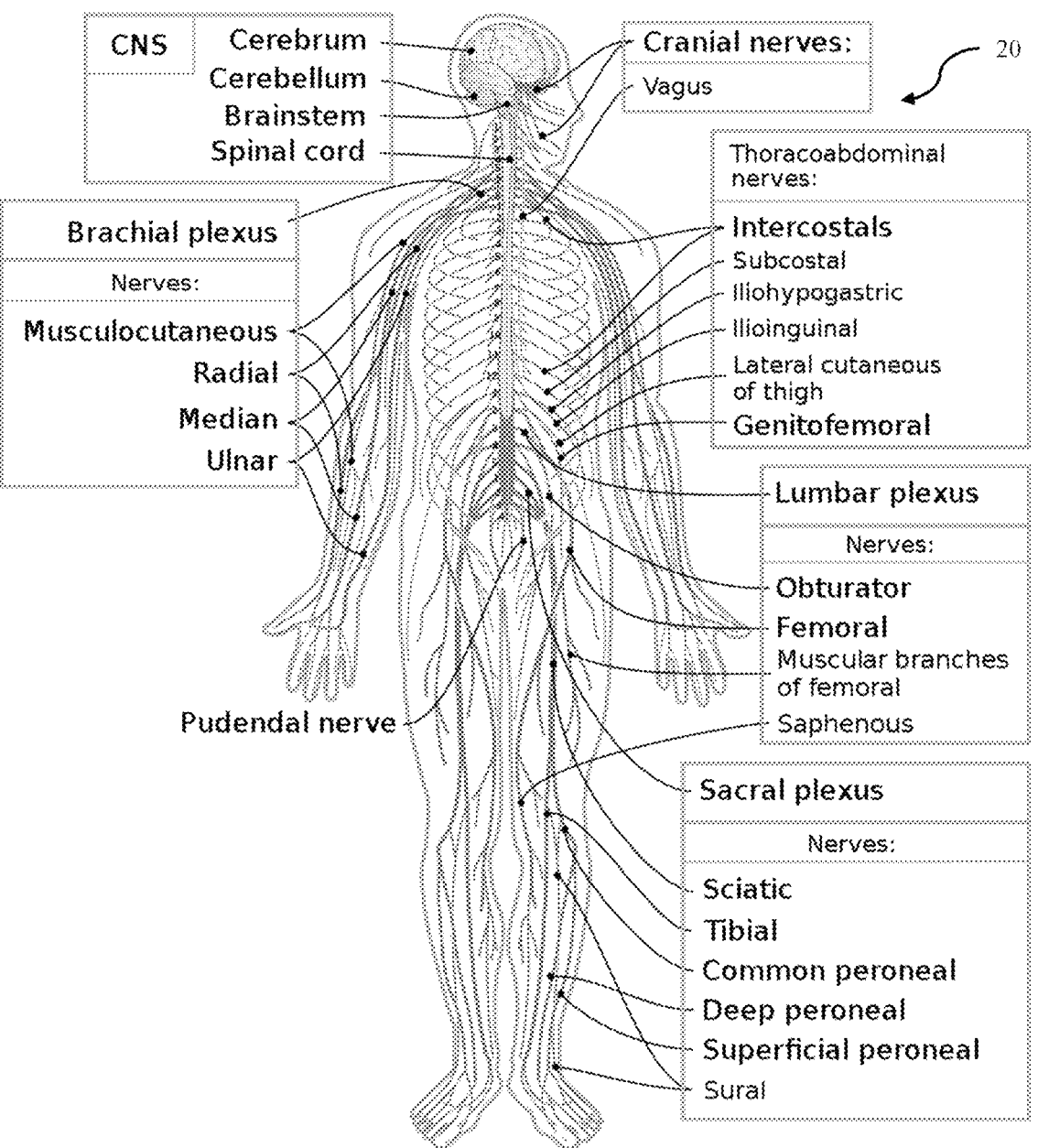
FIG. 2A is a schematic representation of the peripheral nervous system according to an embodiment.

In the following description, like reference characters designate like or corresponding parts throughout the figures.

DESCRIPTION OF EMBODIMENTS

Theories of pain have traditionally attributed the sensory experience of pain to the brain (i.e. a phenomenon of the brain). In more recent times the contributions of psychological and emotional factors to the pain experience have been emphasised, becoming key factors in the development of the biopsychosocial approach for managing persistent pain.

Embodiments of the methods described herein have been developed based on a new hypothesis of the origin of pain, which we call the 'pain channel' hypothesis. This hypothesis has led to development of a novel treatment approach to the management of persistent pain. The clinical outcome has been a persistently pain-free state, represented by a maintained pain score of 0/10 in patient, in a cohort of over 130 patients with various presentations of persistent pain. With complete control of pain through the treatment method, the patients can rapidly return to their premorbid state and level of function. These clinical outcomes thus challenge the current dominant understanding of the role of the brain in pain. That is rather than pain being a construct of the brain, we hypothesise that pain is a peripheral phenomenon, and describe embodiments of a peripherally based treatment method that can reverse the presenting clinical profile of persistent pain. More specifically we hypothesise that the sensory phenomenon of pain is a function of specific sodium channels which are coded for pain and which are part of the subcellular structure of peripheral nociceptive sensory nerves.

Referring now to FIG. 1, there is shown a flowchart of a method 100 for treating a patient in need of pain relief, such as a patient suffering from chronic pain, according to an embodiment. A suspected source location of the persistent pain is first identified and one or more nerves associated with the hypothesised source location are selected 110. Each of the selected nerves is either within the hypothesised source location, in a sensory signal pathway upstream or downstream of the hypothesised source location, or in a sensory signal pathway bounding the hypothesised source location. A regional anaesthetic is then used to temporarily block each of the selected one or more nerves to identify one or more target nerves 120. Regional anaesthesia is thus used as a diagnostic tool to confirm the clinically suspected source location of the persistent pain. The pharmacodynamics of local anaesthetics assists in identifying the sodium channel of the primary nociceptive sensory neuron which is the critical subcellular structure generating the persistent pain. As sodium channel function is as a bioelectromagnetic phenomenon neuromodulation is used to provide long-term pain relief. We hypothesise that the neuromodulation unit produces an electromagnetic field and by implanting the electrode array over the target nerve, and in particular under the stratum corneum near the dermis/hypodermis junction/boundary, an electromagnetic field effect is delivered to the intended sodium channels (of the target nerve) to disrupt signal conduction and create a long-term conduction block (and thus relief of chronic pain). Thus an electrode array of a neuromodulation apparatus is implanted in the patient over each of the at least one target nerves identified. Once implanted (and configured) the neuromodulation apparatus is used to stimulate the electrode array to provide pain relief to the patient 140.

The treatment method was developed and refined in a cohort of over 130 patients suffering chronic persistent pain. The cohort includes patients with a wide variety of presentations, including low back pain, whiplash syndrome, cervicogenic headache, chronic post-surgical pain, facial pain, radicular pain, neuroma pain, vertebral crush fracture, thoracic back pain, phantom limb pain, pelvic pain, visceral pain and cancer survivor pain as outlined in Table 1. The patients range in age from 14 to 100 years and in weight from 45 to 150 kg as outlined in Table 2. Following treatment using embodiments of the method described herein, the pain with which each patient presented was completely controlled with patient reporting pain scores of 0 (out of 10). As a direct consequence of being pain-free, they no longer require analgesic medications and have been able to re-engage in their lives.

TABLE 1

| Sites of presenting pain. | |
| --- | --- |
| Presenting Pain | N |
| Neck pain ± headache | 18 |
| Facial pain | 1 |
| Arm pain | 2 |
| Thoracic spinal pain | 12 |
| Chest wall pain | 9 |
| Upper abdominal pain | 1 |
| Lower abdominal pain post-laparotomy | 2 |
| Genitourinary tract pain | 1 |
| Groin pain post-hernia repair | 1 |
| Low back pain | 73 |
| Pelvic/perineal pain | 3 |
| Leg pain | 1 |
| Foot pain | 1 |
| Lower extremity phantom limb pain | 5 |
| Neck pain ± headache | 18 |
| Facial pain | 1 |

TABLE 2

| Demographic data | |
| --- | --- |
| Male:Female (n) | 41:89 |
| Age range (yrs) | 14-100 |
| Weight range (kg) | 45-150 |

Embodiments and variations of this treatment method, along with associated apparatus will now be described. To assist in understanding of the invention the anatomy and physiology of the peripheral nervous system will be briefly outlined. FIG. 2A is an illustration of the peripheral nervous system 20 which comprises a branch like structure of nerves each of which extend (or branch) out from a nerve root located above or below a vertebrae of the spinal column to specific regions of the body to provide sensory and motor functions. The peripheral nervous system 20 is comprised of sensory neurons (nerve cells) with which comprise receptors located at one (distal) end of tubular axons which extend from peripheral regions of the body towards the spinal cord and brain. There are 31 pairs of spinal nerves comprising eight pairs of cervical nerves (C1 to C8) extending from the first seven vertebrae, twelve pairs of thoracic nerves (T1-T12) each extending from below a respective thoracic vertebrae, five pairs of lumbar nerves emerging from lumbar vertebrae (L1 to L5), five pairs of sacral nerves (S1 to S5) which exit the sacrum at the lower end of the spine (vertebral column), and one pair of coccygeal nerves (Co). These nerves are bundles of nerve fibres and comprise both afferent nerves that transmit signals towards the spine and brain (e.g. pain signals) and efferent nerve fibres that transmit signals away from the spine and brain (e.g. towards muscles). Further as the nerve radiates out the spinal column the nerves may branch and divide (and may recombine) to serve or innervate a specific region of the body. For example the brachial plexus comprising cervical nerves C5 to C8 serve the upper limbs and upper back whilst the sacral plexus (L4 to S4) serve the lower limbs.

Sensory neurons are also referred to as afferent neurons as they transmit signals from peripheral receptors towards the spinal cord and brain. One type of receptor are nociceptors, also known as pain receptors, which detect stimuli such as heat, pressure, or chemicals in peripheral regions of the body. When stimulated these generate an electrical signal known as an action potential which is sent/transmitted along the axon towards the spine and brain. Voltage-gated sodium ion channels are embedded in the cell's plasma membrane and conduction/transmission of the action potential along the axon occurs via voltage-dependent alterations in membrane conductance of the sodium channels. These channels are closed and inactive at rest but undergo structural changes in response to depolarisation, leading to cycling of the channels through activated, inactivated and repriming states.

Figure 2B:
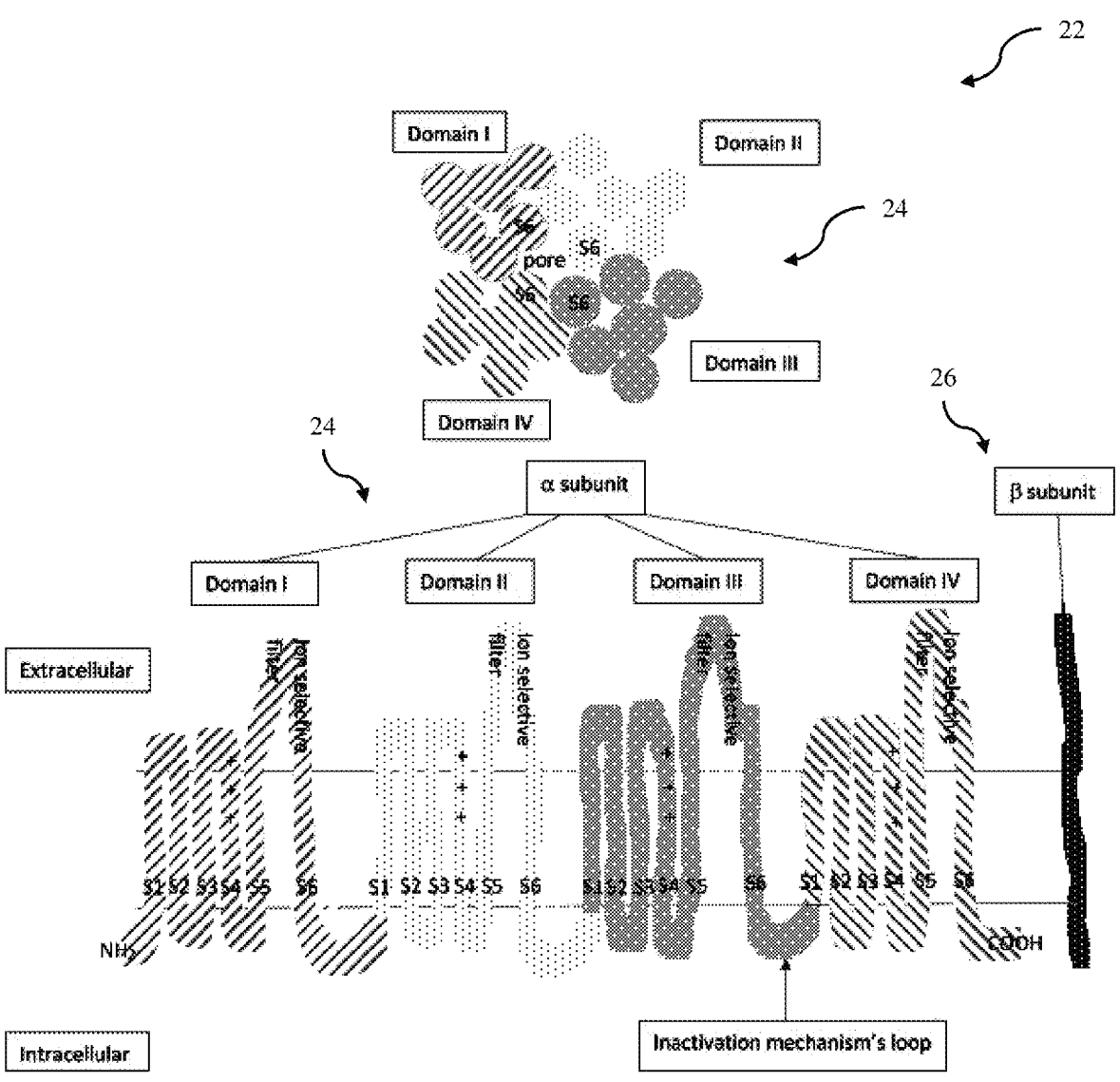
FIG. 2B is a schematic diagram of a sodium channel showing end and side views

The genetics, structure and function of the sodium channel are well known. The sodium channel is composed of alpha and beta subunits, embedded as heterodimeric and heterotrimeric complexes of either 1× alpha and 1× beta, or 1× alpha and 2× beta units in the lipid membrane of the neuronal cell wall. FIG. 2B is a schematic diagram of a sodium channel showing end and side views. There are 9 isoforms of the alpha subunits in humans, designated $Na_v1.1$-$Na_v1.9$ with $Na_v1.7$, 1.8 and 1.9 preferentially expressed in the peripheral nervous system. $Na_v1.7$ exhibits slow closed-state inactivation and activation in response to small slow depolarisations close to resting potential so as to produce its own depolarisation, thereby having the capability of amplifying inputs such as generator potentials and setting the gain on nociceptors. $Na_v1.8$ is relatively resistant to inactivation by depolarisation and recovers rapidly from inactivation, and thus produces repetitive firing in depolarised neurons. $Na_v1.9$ is characterised by very slow activation and inactivation with a large overlap centred near resting potential and contributes a sodium conductance at rest that modulates the excitability of neurons. Under non-pathological conditions the firing properties of nociceptors, like those of most neurons, are maintained within a circumscribed rang, at least in part a function of homeostatic regulation of ion channel expression, post-translational modification, and interactions with binding partners or modulators. Observations of neuronal activity lead to the conclusion that there is molecular and functional remodelling of neurons, whereby these cells selectively activate specific ion channel genes and deploy functional channels to maintain homeostatic tuning of the sodium channels.

The alpha subunit 24 is a protein with approximately 2000 amino acids in its peptide chain. The alpha subunit chain folds into 4 domains (I-IV), with each domain consisting of 6 transmembrane segments (S1-S6), each coil length approximately the width of the membrane. The nonpolar sidechains of each coil length face outward where they readily interact with the lipids of the membrane, and the polar peptide bonds of each coil length face inward. A central pore is created at the extracellular end by the re-entrant loop between the S5 and S6 segments of each of the 4 domains. This re-entrant loop is embedded into the transmembrane region of the channel to form the narrow, ion-selective filter. One residue in this re-entrant loop (Asp/ Glu/Lys/Ala: the DEKA residue) determines ion selectivity. The surfaces above the selective filter contain multiple negatively charged residues on the S5 and S6 loops which act as a shield to exclude anions. S6 segments of each of the 4 domains, arranged as a tetrahelix, form the inner lining of the pore as well as the wider intracellular end of the central pore. The S1-S4 segments form a voltage-sensing domain. The S4 transmembrane segments contain 4-8 repeated motifs of a positively charged amino acid residue, proposed to carry the gating charges in the sliding helix model of voltage sensing.

The four voltage-sensing domains have different numbers of gating-charge residues and are symmetrically associated with the outer rim of the pore module, although each is most closely associated with the pore-forming module of its neighbour, an arrangement believed to facilitate coordinated functioning of all pores. The short intracellular loop connecting domains III and IV of the alpha subunit contains the key hydrophobic sequence (Ile-Phe-Met: the IFM motif) which, in combination with polar residues in 3 other areas— the carboxyl-terminal domain, the voltage-sensing domain, and adjacent transmembrane segments of the channel—form the inactivation mechanism.

A mechanical model of alpha subunit 24 functioning is as follows: with voltage sensing and subsequent activation in the S4 segments there is an outward movement of the S4 segment. Sodium conductance then increases with ionic movement through the selective filter, facilitated by a conformational rearrangement by the S6 tetrahelical bundle. Inactivation of the channel occurs when the short intracellular loop connecting domains III and IV of the alpha subunit bends at a key pair of glycine residues and folds into the pore and blocks it. Inactivation is coupled to activation. In 1952 Hodgkin and Huxley (A. L. Hodgkin, A. F. Huxley, "A quantitative description of membrane current and its application to conduction and excitation in nerves", J Physiol, 117 (1952), pp. 400-544) suggested that ionic permeability changes due to alterations in membrane potential arose 'from the effect of the electric field on the distribution or orientation of molecules with a charge or dipole moment' within the membrane. Molecules with those properties within the structure of the alpha subunit include amino acids with polar properties, charged amino acid residues in key functional positions and strings of connected dipole lining the central channel. Accordingly, alpha subunit activation and deactivation can thus be understood as bio-electromagnetic events, functioning according to the principles of Maxwell's equations.

The beta subunits 26 have a single transmembrane segment, and their role seems to be in localisation and immobilization of sodium channels in specific locations.

Sodium channel dysfunction is a well-recognised phenomenon, and there is a growing body of evidence showing that sodium channelopathies play at least some role in the development of persistent pain states, especially related to the $Na_v1.7$, $Na_v1.8$ and $Na_v1.9$ channels. Inherited erythromelalgia was the first human pain disorder known to be produced by sodium channels, specifically a gain-of-function mutation of the $Na_v1.7$ isoform. $Na_v1.3$ is up-regulated within primary sensory neurons following peripheral nerve injury and displays three properties which can contribute to primary sensory neuron hyperexcitability small ramp-like inputs, rapid recovery from inactivation, and production of a significant persistent current. $Na_v1.7$ and $Na_v1.8$ can interact to produce subthreshold membrane potential oscillations that can trigger ectopic repetitive firing in nociceptors. $Na_v1.7$ and $Na_v1.8$ channels have been shown to accumulate in neuromas, and $Na_v1.7$, $Na_v1.8$ and $Na_v1.9$ contribute to inflammation-induced pain. In the neuroma model, voltage-sensitive sodium channels have been demonstrated to be the fundamental entity responsible for the abnormal electrical activity. $Na_v1.6$ gain-of-function mutations have been reported in trigeminal neuralgia.

Local anaesthetic drugs can be used to generate a neural conduction block by inactivating the sodium channel. This involves several mechanisms. They stabilise the S4 in domain III in an outward, depolarised position and partially stabilise the S4 in domain IV which increases the binding affinity of local anaesthetic in the sodium channel and thereby impede the activation mechanism They also bind to amino acid residues lining the inner surface of the S6 segments in domains I, III and IV, and impede ion penetration. These residues can be accessed in both the activated state of the channel through the central pore, and also in the inactivated state via side-fenestrations in the channel. Finally, they act as allosteric effectors of sodium channel inactivation, i.e., when they bind to residues on the inner pore of the channel, they facilitate inactivation. In the context of this specification, we will refer to the action of local anaesthetic drugs on the sodium channel as a temporary block or a short-term chemical conduction block.

Referring back to FIG. 1 a preliminary step of an embodiment of the method comprises determining or hypothesising a source location of pain in a patient. We will refer to this as the hypothesised source location, or simply the source location. It has been observed that whilst many patients struggle to quantify or describe the quality of their pain, patients are usually able to indicate the location of their pain. Thus determining a source location may comprise taking or reviewing the patient's history, including by asking questions including "Where is the pain?", "Where does it originate?", "Where does it radiate?", and "Is there a recognisable pattern?", etc. Additionally or alternatively, a source location may be determined by performing a physical examination of the patient. The answers to these questions and/or physical observations lead to an initial hypothesized source location which may then be further refined by considering physiological/anatomical aspects. These may include considering the innervation of a structure or region of the body associated with the hypothesized source location, and/or identifying which nerve/s is/are involved or associated with that structure or region.

This investigation is used to determine a hypothesised source location of pain in the patient, e.g., sacroiliac joint dysfunction, cervical facet joint dysfunction, iliohypogastric nerve neurapraxia, etc. One or more nerves associated with the hypothesised source location of pain in a patient are then identified, for example using anatomical and physiological reference material. Regional anaesthesia is used to confirm the hypothesised source location 210 of pain by blocking its sensory supply, the principle being to accurately and specifically identify the involved peripheral nociceptive pathway, which we will refer to as the target nerve (or nerves).

These one or more nerves associated with the hypothesised source location of pain in a patient thus form a nerve test set (i.e. a set of nerves for testing) which are used to identify a set of target nerves for neuromodulation and are one or more nerves that are found to reduce the patient's pain when blocked. Selecting nerves in the nerve test set may include selecting one or more nerve within the hypothesised source location—that is passing through (traversing) the source location/region or terminating in the source location/region (i.e. supplying the source location/region).

Alternatively or additionally nerves in a sensory signal pathway upstream (towards the spinal column) of the hypothesised source location may be selected, as well as nerves in a sensory signal pathway bounding (i.e. adjacent/ surrounding) the hypothesised source location. This may include nerves downstream (to the peripheral) of the hypothesised source location, for example to confirm that blocking of a downstream nerve does not relieve pain.

As outlined above the target nerves are identified (or selected) by selecting a nerve in the nerve test set and temporarily blocking the nerve to determine if blocking the selected nerve reduces the patient's pain. The temporary block may be achieved using a regional/local anaesthetic. The duration of the temporary block may vary from nerve to nerve or patient to patient but in each case the duration is for a time period sufficient to assess if blocking the selected nerve reduces the patient's pain. This may be for a few minutes or few hours, but is preferably an extended time period such as at least 10, 20 or 24+ hours. The time period may be selected based on clinical considerations such as the nature of the patient's condition (e.g. mobility, amount of clinical supervision required, etc) and the duration of the chemical block applied. For extended time periods repeated doses of anaesthetics may be used. This is performed for at least one, and typically many or even all of the nerves in the nerve test set. By blocking nerves supplying or passing through the hypothesised source location, as well as surrounding nerves, one or more target nerves can then be identified based on observed pain relief (due to the temporary block). This may involve specific nerve blocks, e.g., the medial branches of the dorsal rami to investigate facet joint dysfunction, or the lateral sacral branches of the sacral nerve roots to investigate sacroiliac joint dysfunction, or nerve root/s to investigate radicular pain. It may also involve blocking nerves more peripherally to identify/confirm the involved area, e.g., rectus sheath block to identify an entrapment neuropathy of the abdominal wall, followed by more specific blocks to identify the actual nerve roots involved. Typically enough nerves are blocked to allow identification of target nerves. Examples of diagnostic nerve blocks with resultant diagnoses are shown in Table 3. If multiple nerves are found to each provide pain relief then one or more (or all) of these nerves may be selected. For example the nerve which provides greatest pain relief or based on clinical considerations (e.g. is most easily accessed or least likely to generate complications) may be selected from the nerve test set as the target nerve. Alternatively some combination of target nerves may be selected from the nerve test set, for example based on clinical considerations. The target nerve set is thus a subset of the nerve test set, and may be a single nerve or multiple nerves. That target nerve set may also comprise all the nerves in the nerve test set.

TABLE 3

Examples of diagnostic nerve blocks with resultant diagnoses

| Diagnostic Nerve Block/s | Diagnosis |
|---|---|
| Greater occipital nerve block | Occipital neuralgia |
| Cervical medial branch blocks | Cervical facet joint dysfunction |
| Superficial cervical plexus block | Superficial cervical plexus neurapraxia |
| Cervical epidural block | Cervical radiculopathy |
| Thoracic nerve root block | Thoracic radiculopathy |
| Thoracic medial branch blocks | Thoracic facet joint dysfunction |
| Rectus sheath block | Entrapment neuropathy of abdominal wall |
| Thoracic nerve root block/s | Entrapment neuropathy of specific abdominal wall nerve/s |

TABLE 3-continued

Examples of diagnostic nerve blocks with resultant diagnoses

| Diagnostic Nerve Block/s | Diagnosis |
|---|---|
| Combined lateral sacral branch blocks & sacroiliac joint injection | Sacroiliac joint dysfunction |
| Lumbar epidural injection | Spinal stenosis |
| Sciatic nerve block | Lower extremity phantom limb pain |
| Posterior tibial nerve block | Posterior tibial nerve neurapraxia |
| S1 nerve root block | Neurapraxia of medial plantar branch of posterior tibial nerve |

Figure 2C:
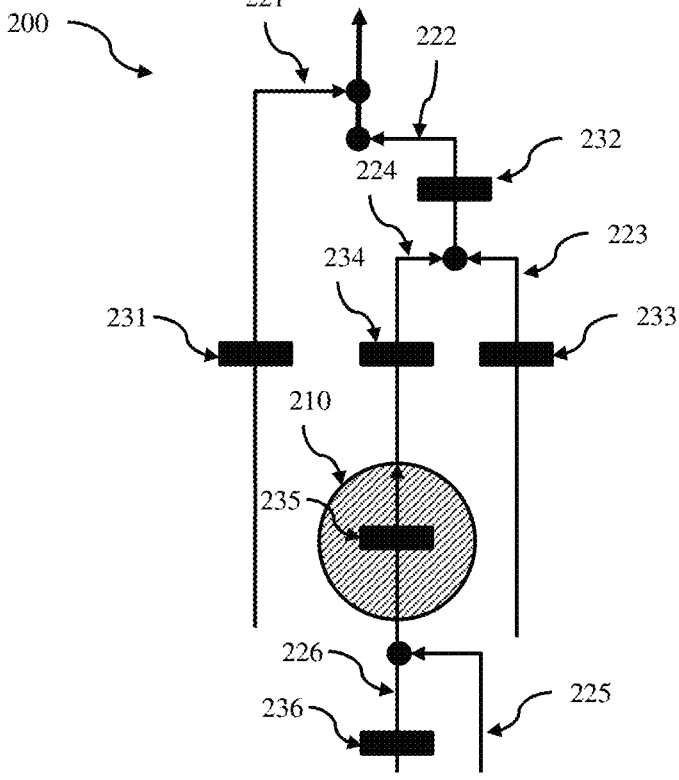
FIG. 2C is a schematic representation of a nerve signalling network around a source location according to an embodiment.

This is further illustrated in FIG. 2C schematic representation of a nerve signalling network 200 around a source location 210 according to an embodiment. For the sake of clarity we will refer to directions in the afferent context (i.e. returning signals to the spinal cord/brain) however the nerves may be strictly afferent, strictly efferent or include both afferent and efferent nerves. The source location 210 is bounded by a first nerve 221 that pass adjacent to the source location 210 (and returns to the spinal cord an onward to the brain) and a third nerve 223 that also pass adjacent to the source location (but distal from first nerve 221). A fourth nerve 234 passes through the source location with a branch point after the source location into fifth nerve 225 and sixth nerve 226 (or nerve branches). The third 223 and fourth 224 nerves (branches) join together to form second nerve 222 which returns to the spinal cord an onward to the brain. In this context fourth nerve 224 passes though the source location, and may comprise branches that terminate in the source region 210. Sixth nerve 226 is downstream of the source location whereas second nerve 222 is upstream of the source location.

The rectangular squares represent anaesthetic blocks which block the sensory supply to the target region, and so prevent nerve signals downstream of the block from reaching the spinal cord and brain. As illustrated in FIG. 2B, first block 231 can be used to block the first nerve 221, second block 232 can be used to block second nerve 222 and all nerves downstream of this block (nerves 223, 224, 225, and 226). Third block 233 is used to block third nerve 233. Fourth block 224 blocks fourth nerve 224 upstream of the source location whilst fifth block 235 blocks the fourth nerve 224 within the source location 210. Both fourth 234 and fifth blocks 235 also block fifth 225 and sixth 226 nerves. Sixth block 236 is downstream of the source location 210.

Each selected nerve is temporarily blocked for a time period sufficient to assess if blocking the nerve reduces the patient's pain. This may be assessed by using a pain score on some range e.g. pain on the range of 0 to 10, where 0 is no pain and 10 is the worst possible pain. This time period may be short such as a few minutes, an hour, or it may be longer such as several hours, or at least 12 or even 24 hours to confirm extended reduction of pain. This may involve repeated doses of local anaesthetic to the target nerve. Pain may be assessed periodically (e.g. via pain scores) during the time period, or an overall assessment may be made after the block is removed. A target nerve may be identified by a significant reduction in pain score for an extended time period. For example this may a reduction to a pain score of specific amount such as a predetermined number of points (e.g. 4 points on a 10 point scale) or a predetermined percentage such as 30% or 40%, or reduction to (or below) a predetermined threshold level such as 2, 1, or 0. In one embodiment the target nerve is identified as a nerve which provides complete control of pain, that is a pain score of 0 for a predetermined time period such as 1 hour, 12 hours or 24 hours (or more). In other embodiments a reduction to a pain score of 0 for a predetermined time period within the expected efficacy duration of the anaesthetic. For example the anaesthetic may be expected to be effective for four hours. In this case a reduction to a pain score of 0 for a 2 hour time period, such as hours 2 and 3 may be used to assess pain reduction. In the case that total reduction is not achieved for an extended time period, a target nerve may be selected if it provides a significant reduction to below a threshold pain score for an extended time period, such as remaining below 2 for 1, 2, 3, 4, 6, 12, or 24 hours, or some other extended time period or expected efficacy duration.

This short-term diagnostic result is then converted to long-term complete control of pain using a neuromodulation apparatus. A neuromodulation apparatus is a device comprising a stimulator circuit connected to and used to drive an electrode or electrode array. Each electrode (or electrode array) of the neuromodulation apparatus is implanted in the patient in the skin in order to overlie the target nerve(s) and once implanted (i.e. in use) the electrode array is stimulated by the neuromodulation apparatus to provide pain relief to the patient (step 130 in FIG. 1). As discussed below the electrode array may be implanted in the skin such that it is under the stratum corneum and in the dermis or hypodermis, with location in the hypodermis generally preferable. However placement could also be under the skin such as adjacent the hypodermis or possibly deeper. By programming the neuromodulation apparatus to provide a continuous stimulation block to the respective target nerve (via continuous stimulus signals to the electrode array), continuous pain relief can thus be provided to the patient.

Figure 3A:
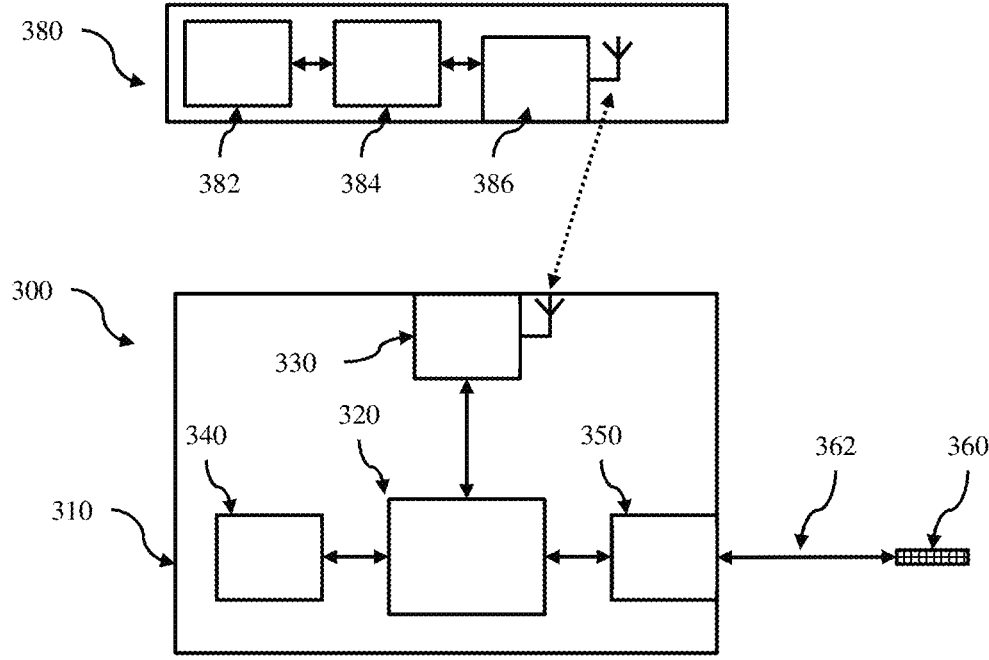
FIG. 3A is a schematic view of a neuromodulation apparatus.

FIG. 3A is a schematic view of an embodiment of a neuromodulation apparatus 300 comprising a control unit 310 which houses a control circuit 320 such as a microprocessor and memory, a wireless communications module (also known as a telemetry unit) 330, a power supply 340 which may include a battery, and a stimulator circuit 350. In some embodiment the control unit is an implantable control unit with a sealed hermetic housing. An electrode 360, which may be a single electrode or typically an electrode array comprising a plurality of spaced apart electrodes, is electrically connected to the implantable control unit 310 via an electrical lead 362 which comprises one or more wires sheathed in a protective covering with one or more electrodes or an electrode array at a distal end of the lead. The proximal end of the lead may be connected to the stimulator 350 via a feed through connector in the housing. In some embodiments multiple electrodes and associated leads are connected to the control unit 310. Typically each lead drives a separate electrode or electrode array. Two or more electrodes/leads may be connected and these may be arranged in pairs of electrodes/leads. The power supply 340 may comprise a long life battery, a rechargeable battery, and/or a charging coil to allow wireless power delivery or wireless recharging of a battery.

The control circuit such as a microprocessor or microcontroller is configured to control operation of the device including operation of the stimulator. The various modules may be mounted on a PCB. The control circuit may comprise an integrated circuit and discrete components; a microprocessor, associated memory and discrete components. In one embodiment an integrated microcontroller board integrating the microprocessor, memory, I/O circuits and wireless communication components can be used. In some embodiments the stimulator circuit may be a separate module under control of the microprocessor including discrete components and/or an integrated circuit or a microcontroller board (incorporating the microprocessor) may be part of, or form the stimulator circuit, for example by generating stimulator signals on output ports to which the leads 362 are connected to. The control circuit or microprocessor may be pre-programmed to operate the stimulator in which case the wireless communications module 330 could be omitted. Preferably a wireless communications module 330 is included to allow the control circuit to be externally programmed by an external programming device 380 (via the wireless communications module 330). This external programming device 380 may comprise a user interface 382, a processor 384 and a wireless communications module (or telemetry unit) 386 for communicating with the wireless communications module 330 in the neuromodulation apparatus. This allows a clinician to implant the neuromodulation apparatus, and then later configure the operation of the neuromodulation apparatus, as well as allowing post implantation adjustment/reconfiguration. This may include control/selection of the pulse frequency, amplitude and width of the stimulation signals. The stimulator is configured to generate a range of stimulation signals. For example one stimulator (Medtronic Intellis Model 97715 Implantable Neurostimulator, and associated Modell 97725 Wireless External Neurostimulator) is configured to produce pulses with pulse rates/frequencies in the range of around 40 to 1200 Hz, pulse widths in the range of 60 to 1000 microseconds and amplitudes in the range of 0-25 mA per electrode (e.g. up to 100 mA with a 4 electrode array). These are adjustable in set increments (e.g. 5 Hz, 10 microsceconds, and 0.1 mA). The external programming device may be configured with one or more template programs which define initial settings (e.g. pulse rate/frequency, pulse width and pulse amplitude). The external programming device provides a user interface that allow a user to select an initial program and then to modify the initial settings. The settings may be sent to the stimulator and then stored, or the stimulator may also store the program and the external programming device indicates the program and variations to settings. For example one initial program is a pulse rate/frequency of 40 Hz, pulse width of 1000 microseconds and an amplitude of 0 mA. The amplitude may then be increased to a desired level, and the other settings may be further adjusted and then the final customised program is stored. These settings are then stored by the stimulator for use. Typically these are set by the clinician, typically in consultation with the patient, and in some embodiments the patients are allowed to adjust some of the parameters such as amplitude. Thus a further step in the method may comprise programming or configuring the neuromodulation apparatus to provide a continuous conduction block (i.e. continuous stimulus signals to the electrode array) to the respective target nerve to provide continuous pain relief to the patient. A range of commercial neuromodulation apparatus (and associated external programming device) may be used. This include those in the Medtronic Intellis Neurostimulation product range such as Models 97715 and 97716 Implantable Neurostimulators, and the Model 97725 Wireless External Neurostimulators.

Figure 5:
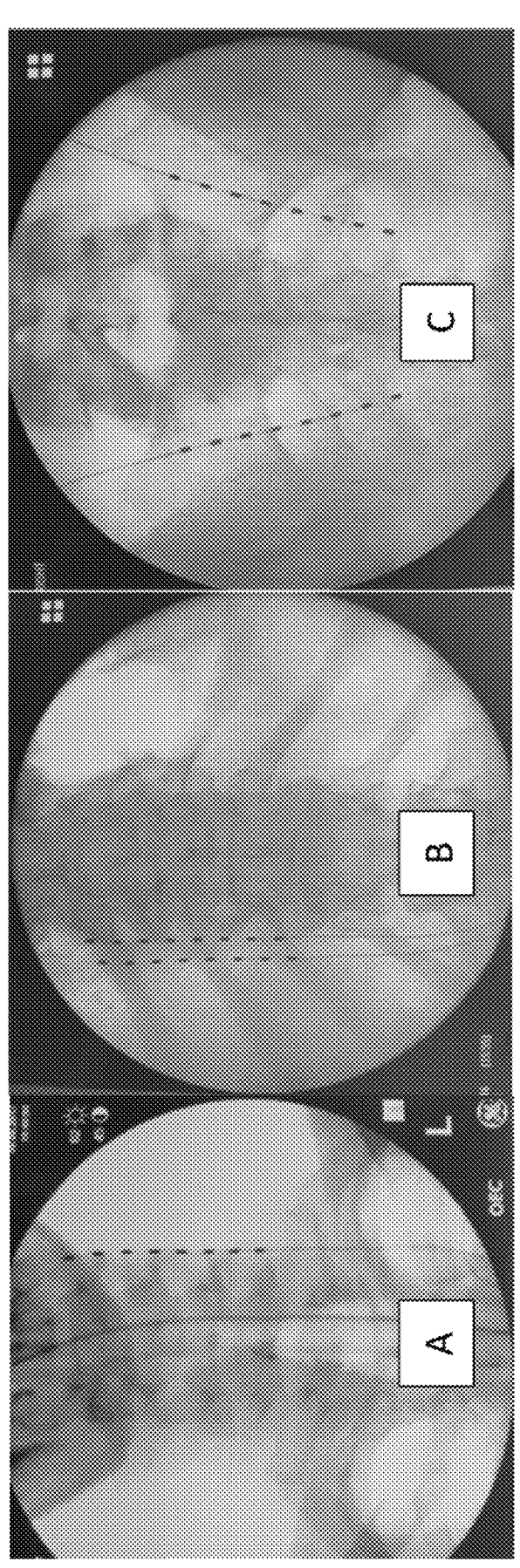
FIG. 5 shows images of the placements of neuromodulation electrodes and associated leads in three patients.

In some embodiments the complete neuromodulation apparatus (control unit 310 and electrode/leads 360/462) is implanted in the patient, or alternatively just a portion of the lead 362 comprising the electrode array 360 are implanted in the patient, with the remaining portion of the lead(s) and main control unit 310 located outside of the body. In some embodiments the electrode is an externally powered implantable array, in which just an electrode module is implanted which receives wireless power signals from an external transmitter driven by the (external) control unit 310. FIG. 5 shows representative placements of neuromodulation electrodes (leads): Image A shows the left cervical facet joint dysfunction, image B shows Right thoracic radiculopathy and image C shows Bilateral sacroiliac joint dysfunction.

The use of neuromodulation for analgesia was pioneered by the neurosurgeon Dr Norman Shealy and his colleagues in the 1960's. The predominant use of neuromodulation for analgesia is dorsal column stimulation in which an electrode array is placed in the epidural space and pulses with frequencies in the range of 40 Hz to 100 Hz are used to 'stimulate' the dorsal column. More recently other applications have been explored including placement of the electrode array in the subcutaneous tissues 'within the area of pain', a technique known as peripheral nerve field stimulation, as well as exploring higher frequencies (up to 10 kHz) and stimulation patterns. The mechanism of action for both of these techniques is more often explained by reference to the 'gate control' theory of Melzack and Wall. In this scenario electric current from the neuromodulation unit stimulates large non-nociceptive sensory fibres, which subsequently inhibit small nociceptive fibres through interconnections within the substantia gelatinosa of the dorsal horn of the spinal cord and thereby modulate the afferent nociceptive signal to the brain. However, there are two reasons why this mechanism of action is unlikely to be correct—firstly, experimental evidence for such an effect between these sensory fibre types is lacking; secondly, the electrical output of the neuromodulation unit is not in the form of an electric current.

Figure 3B:
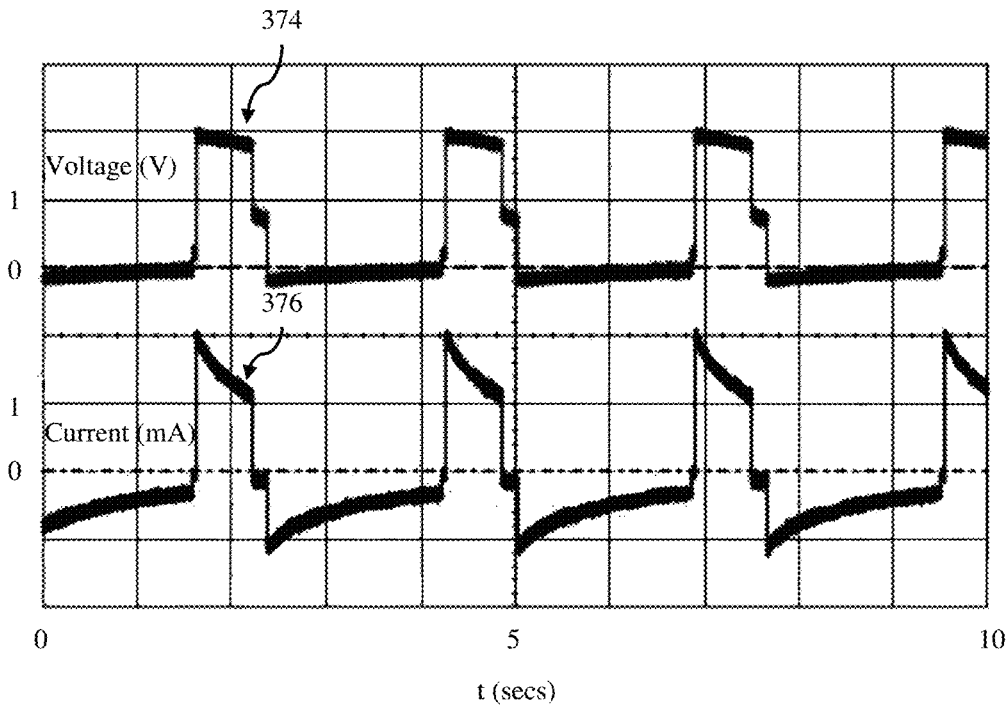
FIG. 3B is a plot of the voltage pulses and current pulses generated by a neuromodulation unit.

As illustrated in FIG. 3B, a neuromodulation unit produces a digital pulsatile waveform with a square wave configuration. FIG. 3B shows a plot of the voltage pulses (or waveform) 374 and current pulses (or waveform) 376 generated by a neuromodulation unit. Effectually this means that there is an intermittent voltage difference applied across the electrode array rather than an electric current. A time-varying voltage difference across the electrode array is a source of time-varying electric and magnetic fields, the inter-relationship between these being described by electromagnetic theory and expressed mathematically by Maxwell's equations:

Gauss' law:

$$\Phi_E = \oint E \cdot dS = \sum \frac{Q}{\varepsilon_0}$$

which defines that the net electric flux across a closed surface is proportional to the amount of charge enclosed;

Gauss' law for magnetism: $\Phi_B = \oint B \cdot dS = 0$ which defines that the net magnetic flux across a closed surface is zero;

Faraday's law of Magnetic Induction:

$$\epsilon = -\oint \frac{d\Phi_B}{dt} - = -\frac{d}{dt} \oint B \cdot dS = \oint E \cdot dl$$

which defines that time varying magnetic fields induce an electric field; and

Ampere's law with Maxwell's correction:

$$\oint B \cdot dl = \mu_0 \left( I + \varepsilon_0 \frac{d}{dt} \oint E \cdot dS \right)$$

which defines that a magnetic field can be generated by an electric current and/or time varying electric field.

The combination of Faraday's law of Magnetic Induction and Ampere's law with Maxwell's correction lead to the observation that a time varying magnetic field induces an electric field and vice versa. This allows the generation of a self-sustaining (and propagating) electromagnetic wave that travels at the speed of light in a vacuum. Additionally Maxwell's equations define that (at least theoretically) electromagnetic fields extend indefinitely throughout space and can affect the behaviour of charged objects in the vicinity of the field. The human body however is a finite inhomogeneous conductor with its own particular electromagnetics characteristics and thus within the human body an electromagnetic field transmits by volume conduction (see J. Malmivuo, R. Plonsey, "Volume source and volume conductor", Bioelectromagnetism: principles and applications of bioelectric and biomagnetic fields, Oxford, New York (1995), pp. 133-147).

The application of electromagnetic theory already has an established place in medical practice, albeit as a diagnostic rather than a therapeutic tool, e.g. it forms the theoretical basis of electrocardiography. The neuromodulation unit transmits a pulse frequency of around 40 Hz which generates an electromagnetic field around the electrode array. This can be seen on an oscilloscope (FIG. 3B)) or observed as interference on a concurrently run electrocardiogram. Various investigators have utilised intermittent voltage differences applied across an electrode array in neurophysiological models. Eccles et al. ("The effect of electric polarisation of the spinal cord on central afferent fibres and on their excitatory synaptic action", J Physiol, 162 (1962), pp. 138-150) demonstrated depressed excitatory action in presynaptic afferents, while da Costa et al. ("Can electromagnetic radiations induce changes in the kinetics of voltage-dependent ion channels?", Cell Mol Biol, 48 (2002), pp. 477-583) and Bhadra and Kilgore ("Direct current electrical conduction block of peripheral nerve", IEEE Trans Neural Syst Rehabil Eng, 12 (2004), pp. 313-324) demonstrated deactivation of sodium channels in an axonal model. Kent et al. demonstrated suppression of afferent neuronal activity in a dorsal root ganglion model. With the exception of Da Costa et al., the concept of intermittent voltage differences producing an electromagnetic field has not been considered.

Without being bound by a particular theory the inventor hypothesises that neuromodulation produces analgesic effects by deactivating sodium channels in nociceptive sensory axons through the effect of an applied electromagnetic field. In the context of this specification we will call this effect a long-term electronic conduction block. A pain-free state has been achieved in a cohort of patients summarised in Table 1 by applying such long long-term electronic conduction block. This is based on the following mathematical model to the use of neuromodulation. In producing an electromagnetic field, the electrode array of the neuromodulation unit is a considered a transmitting antenna. In antenna theory, a Cartesian co-ordinate system is used to describe array position and radiation pattern. In the context of this specification, this is adapted to anatomic correlates which are referenced to the neural target:

'x'—medial/lateral positioning of the electrode array relative to the neural target;

'y'—cephalad/caudad positioning of the electrode array relative to the neural target; and 'z'—the depth of the electrode array from the skin surface.

During implantation, the imaging modalities of fluoroscopy and ultrasound facilitate placement of the electrode, with standard antero-posterior fluoroscopic imaging providing 'x' and 'y' co-ordinates and ultrasound imaging providing the 'z' co-ordinate. The 'x' and 'y' coordinates are used to position the array such that 'x'='y'=0 (prone position; array overlying neural target). This places the array at the centre of a radiating electromagnetic field with the neural target at radius 'r' to deliver maximal field effect to the target.

We can apply Maxwell's law as follows.

The maximal electric flux can be calculated using Gauss's law:

Gauss' law:

$$\Phi_E = \oint_J E \cdot dS = \sum \frac{Q}{\varepsilon_0}$$

which defines that the net electric flux across a closed surface is proportional to the amount of charge enclosed;

cos θ=angle at which the direction of the electric field intersects dS;

cos 90°=0, $d\Phi_E$=0, cos 0=1, $d\Phi_E$=EdS $d\Phi_E$ is maximal when source charge Q is at the centre of a hypothetical sphere of radius r, and dS is on the surface of the sphere. In this scenario, the E field travels radially cos θ=1 and so $d\Phi_E$=EdS i.e., maximal electric flux.

Accordingly, the electrode array is treated as the source charge with the specified neural target at dS.

When electric field strength is independent of distance from charge source then for a cylindrical area centred in the middle of a large flat plate, and through which the electric field from a charge source passes in parallel fashion, we find (applying Gauss's law):

dS=$2\pi r^2$ (the field will pass through both ends of the cylinder),

Q=σdS=σ$\pi r^2$ where σ is charge density, $$\therefore d\Phi_E = E2\pi r^2 = \frac{\sigma \pi r^2}{\varepsilon_0},$$

$$\therefore E = \frac{\sigma}{2\varepsilon_0}$$

i.e., E is independent of height of cylinder.

With the charge source immediately adjacent to the skin, the latter effectively acts as the hypothetical large flat plate, and E is independent of radius 'r' in Gauss' law above.

When magnetic flux is independent of distance from charge source:

B∝I/r where I=current, r=distance from wire,

B=$\mu_0$/2$\pi$×I/r where σ is charge density, $\oint$ B·dl=B2$\pi$r,

∴ by substitution $\oint$ B·dl=$\mu_0$I (Ampere's law).

Magnetic flux is independent of distance from charge source, and the electromagnetic field extends continuously.

The work done to close the activated sodium channels can be derived from Faraday's law of Magnetic Induction ∈∝E. The work done, or energy required, to close the channels is proportional to the strength of the electric field, which is a function of the amount of charge delivered to the electrode array. The amount of delivered energy to achieve complete relief of pain equals the energy required to deactivate the sodium channels, or the kinetic energy of channel deactivation. Thus once the electrode is in position in the skin (or under the skin such as adjacent the hypodermis) to overlie the target nerve electromagnetic energy is titrated (using the neuromodulation apparatus) until a pain-free state is attained (e.g. by controlling pulse width, frequency and/or amplitude).

Figure 4:
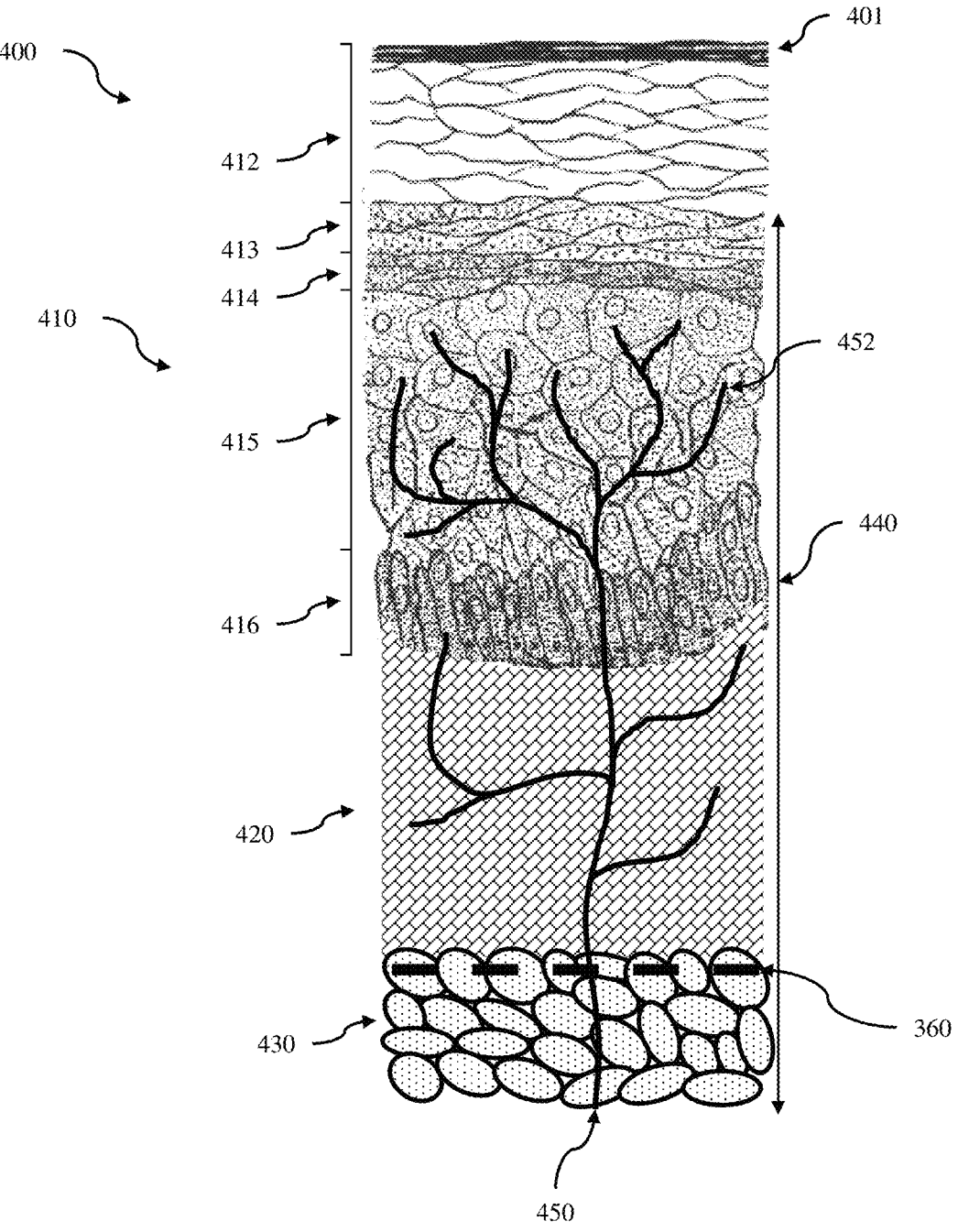
FIG. 4 is a schematic sectional view of the upper layers of the skin.

During the implantation procedure the electrode array is implanted in (or less preferably, under) the skin to provide an electric field on the target nerve. FIG. 4 is a schematic sectional view of the upper layer of the skin 400 extending down from the surface of the skin 401 and showing the epidermis 410, the dermis 420 and the top portion of the hypodermis (or subcutis) 430. The top most layer of the epidermis is known as the stratum corneum 412 comprised of composed of 10 to 30 layers of anucleated corneocytes (differentiated keratinocytes) and lipids which form the outer skin barrier. The stratum lucidum 413 is a narrow layer which is only found in the palms and soles (providing a thicker skin layer in these regions). The next layer is stratum granulosum 414 which is a granular layer of keratinocytes which have lost their nuclei and their cytoplasm. The next layer is the stratum spinosum 415 or spinous layer formed mainly of keratinocytes along with Langerhans cells. The final lower most basal layer is the stratum basale 416 comprised mostly of proliferating and non-proliferating keratinocytes attached to the basement membrane, along with some Melanocytes and Merkel cells. Below the epidermis 410 is the dermis 420 comprising dense irregular connective tissue Below the epidermis 410 is the dermis 420 comprising dense irregular connective tissue comprised of fibroblasts, macrophages, and mast cells along with collagen, elastic fibres, and an extrafibrillar matrix. The dermis 420 is tightly connected to the epidermis 410 via the basement membrane. The hypodermis 430 is located below the dermis 420 and is mostly comprised of fibroblasts, adipose cells, and macrophages which form a loose connective tissue. The dermis 420 and hypodermis 430 are penetrated blood vessels, lymph vessels and nerve fibres including nociceptors 450 which are afferent nerve fibres ending in free nerve ends 452 which function to detect pain. A stimulus at the free nerve end 452 travels along the nerve fibre to the brain via the spinal cord where the signal is recognised as a pain signal.

In one embodiment the 'z' depth of the electrode array 360 is selected to be under the stratum corneum 412 in region 440 including the dermis 420 and hypodermis 430. It has further been found that placement (implantation) of the electrode array 360 in the hypodermis below the stratum corneum 412 and in particular around the junction of the dermis 420 and hypodermis 430 assists in achieving maximal analgesic effect. At this depth the energy required to achieve maximal analgesic effect is minimised which enables greater tolerance of the neuromodulation unit's electrical energy output. This is illustrated in FIG. 4, which shows the electrode array 360 implanted in the hypodermis 430 adjacent the dermis 420 (i.e. so it is on the distal side of the dermis and stratum corneum with respect to the surface of the skin 401). This positioning of the electrode array 360 as close as possible to the boundary between the dermis 420 and hypodermis 430 was found to minimise any unpleasant sensations such as can occur with intradermal placement of the array and maximised the analgesic effect. Note that whilst placement of the electrode array in the hypodermis was found to be preferable, placement in the dermis 420 will still provide a therapeutic/analgesic effect. However placement in the dermis generated uncomfortable/unpleasant stinging sensations in some patients and thus whilst effective, is less preferable. Placement of the array deeper than the hypodermis is also possible and will still provide a therapeutic/analgesic effect. However it was found that the effect diminishes over the course of several months requiring replacement or adjustment of the array, and as such placement deeper than the hypodermis whilst effective, is less preferable.

Without being bound by theory it is hypothesised that the skin layers are associated with electromagnetic scatter, in particular backward scatter at the stratum corneum. Scatter occurs when the emitted field is forced to deviate from its straight trajectory by the medium through which it is passing. It is believed that the stratum corneum, due to its unique electrical and electromagnetic properties may act rather like a paraboloid reflector and hence increase directivity of the radiating electromagnetic field towards the target nerve. The positioning of the electrode array 360 under the stratum corneum 412 and in the hypodermis 430 is believed to provide sufficient distance (or stand-off) to provide a stable (electromagnetic) field on the target nerve which we believe is likely important to the stability of the field effect on the sodium channel.

As noted previously once implanted the neuromodulation apparatus can be programmed or configured to provide a continuous conduction block to the respective target nerve to provide continuous pain relief to the patient (i.e. a long term conduction block), such as by a clinician using an external programming device 380 to configure the implanted neuromodulation apparatus. In some embodiments the electrodes could first be implanted with the neuromodulation unit located outside of the body to allow configuration. Once appropriate settings have been confirmed to provide pain relief, a neuromodulation device may be permanently implanted. Alternatively the electrodes could be removed and new electrodes reinserted and the process repeated.

In one embodiment the neuromodulation device comprises a memory storing a set of pre-configured programs which may be used as a starting point for determining an optimal therapeutic configuration. This may include determination of cathodic or anodic pattern specific to the individual, variation in duration of pulse, frequency of pulse delivery, and amount of energy delivered per pulse. In some embodiments this is programmed in consultation (i.e. using feedback) from the patient to maximise efficacy and minimise intolerance of the electromagnetic field source. This may then be set until it is reconfigured by the clinician (i.e. set and forget). In some embodiment the patient may be allowed to adjust the configuration, or some of the configuration settings such as amplitude using a patient interface on the external programming device 380. It requires physical and cognitive ability, cooperation, understanding and a willingness of the patient to manipulate the programs and to interact with the equipment, as opposed to a 'set and forget' approach as is employed with a cardiac pacemaker for example. Engagement of the patient and their carers for self-management was found to enhance the success of this therapy (as is recognised in other positive treatment outcomes), allowing the patient to dynamically adjust the neuromodulation apparatus to maximise efficacy and minimise intolerance of the electromagnetic field source. For example in one embodiment an initial program template is selected, such as a pulse rate/frequency of 40 Hz with a pulse width of 1000 microseconds (1 ms) and an initial amplitude of 0 mA. The amplitude is then increased and set to a level where the patient just perceives the sensation and is at a level to effectively eliminate pain. The pulse width and rate may then be adjusted (based on patient feedback) to render the sensation of the neuromodulation more comfortable. For example, a small reduction in the pulse width setting can mitigate a stinging sensation, and increasing the rate can render the sensation less perceptible.

Embodiments of the method thus links short-term chemical conduction block for diagnostic purposes with a long-term electronic block for therapeutic purposes. The sodium channel is the targeted subcellular element and is a component of the nociceptive primary sensory neuron which extends from the dorsal horn of the spinal cord through the dorsal rootlets, dorsal root ganglion, nerve root, dorsal and ventral rami, plexus, peripheral nerve trunk, sensory branches, to the peripheral nerve ending. In theory this provides multiple sites and opportunities for effecting the required conduction blocks. However, the point targeted for conduction block along this neural pathway is preferably selected based on the following criteria:

specificity within neuroanatomic organisational principles;

accessibility for application of both short-term chemical and long-term electronic conduction blocks; and stability of site for implantation of the electrode array.

As an example of this process, the specificity of segmental organisation is utilised for pain of somatic origin, the nerve root being the fundamental identifier at single sensory level of an involved nociceptive primary sensory neuron. Sensory nerves such as the medial branches of the dorsal rami of the spinal nerves or the lateral sacral branches provide specificity, selectivity and simplicity, and are targeted for the diagnosis of facet joint dysfunction or sacroiliac joint dysfunction respectively. For other sources of pain of musculoskeletal or nerve origin, identifying the involved ventral root/s is the ultimate goal, as the segmental organisation at this point of the neural pathway provides specificity and simplicity. It may however be necessary to initially block more distally to clarify a source of pain, e.g., rectus sheath block in the setting of abdominal pain, which can distinguish between an abdominal wall and intra-abdominal source of pain. It is then necessary to identify the specific spinal nerves involved in the pathway. Accessibility to the nerve root is achievable posteriorly at the point of its emergence from the intervertebral foramen, where there is no interference by bone for either passage of a needle or transmission of the electromagnetic field. The subcutaneous tissues of the back provide stability of site to minimise movement of the array during the healing phase and hence prevent lead migration. Using this approach neural targets from C2-S4 have been identified using short-term chemical block, and then long-term electronic block has been applied to the same site for long-term therapeutic effect. Table 4 lists several exemplary case studies showing efficacy of embodiments of the method described herein.

TABLE 4

| Exemplary case studies of patients treated using an embodiment of the method described herein | | | | | | | |
| Presenting | | Pre-Treatment | Post Implantation | Stimulator settings | | | Duration of Treatment |
| Pain | Target Nerve | Pain Score | Pain score | Hz | μs | mA | (years) |
| Phantom limb pain | Sciatic nerve | 9/10 | 0/10 | 60 | 910 | 1.1 | 5 |
| Post hernia pain | Ilioinguinal nerve | 5/10 | 0/10 | 40 | 850 | 0.5 | 2 |
| Low back pain | Lateral sacral branches | 8/10 | 0/10 | 40 | 1000 | 1.7 | 4 |
| Chest wall pain | Thoracic medial branches | 7/10 | 0/10 | 40 | 970 | 1.3 | 3 |
| Facial pain | Maxillary nerve | 7/10 | 0/10 | 40 | 970 | 0.7 | 1.5 |

Table 4 illustrates the efficacy of the embodiments of the treatment method and show a persistent long term reduction in chronic pain for a wide range of chronic pain sources/presentations.

Complete control of persistent pain in a sustained fashion provides a unique opportunity to observe the individual without pain. It was noted that the desire to re-engage with life is universally present, as is the desire to discontinue analgesic and anti-neuropathic medications. Mental health improves simultaneously with relief from pain and with regeneration of hope, a phenomenon which has been noted previously. Indeed, the recovery of emotional stability with relief of pain is so marked that we have concluded that pain is not an emotional experience per se but rather that it provokes an emotional response. In brief, stopping the pain stops the response.

Embodiments of the method describe herein are based on the hypothesis that the sensory phenomenon of pain comes from the specific sodium channels which are coded for pain and which are part of the subcellular structure of the nociceptive primary sensory neuron. This hypothesis derives from the inventors' work in persistent pain and we refer to it as the 'pain channel' hypothesis of the origin of pain. A large and growing cohort of persistently pain-free patients from a wide spectrum of presentations (see Table 1) represents a unique and important outcome and requires explanation. Regional anaesthesia has been used to confirm the source of the persistent pain which has been deduced from the history and physical examination. The pharmacodynamics of local anaesthetics identify the sodium channel of the primary nociceptive sensory neuron as the critical subcellular structure generating pain. Sodium channel function has been recognised as a bioelectromagnetic phenomenon and susceptible to the influence of an applied electromagnetic field. We have applied electromagnetic theory to understand the mechanism of action of neuromodulation which to our knowledge has not previously been considered. Principles of applied anatomy underlie determination of the site for coordinating the short and long-term conduction blocks. Mathematical modelling lends precision to the process of placing the electrode array. The linking of short-term chemical and long-term electronic conduction blocks takes advantage of their commonality of site of action to reproduce the initial short-term pain relief on a long-term basis. In this context neuromodulation can be viewed as electronic local anaesthetic. The above process thus differs from that employed in peripheral nerve field stimulation, a difference we believe is reflected in our clinical outcome.

Whilst others have identified the sodium channel of the nociceptive primary sensory neuron as a potential target in the management of persistent pain using pharmacological and gene-based strategies, no one else to date has achieved complete and sustained relief of pain across such varied presentations. This would infer that the applied electromagnetic field has been effective in spite of differences in isoform or phenotype. Variations in programming of the electrode configuration may however reflect those differences.

Our hypothesis contrasts with the traditionally held view that pain is a phenomenon of the brain, a view which has been supported by studies demonstrating apparent changes in central nervous system morphology in chronic pain states. A peripherally based strategy such as ours should therefore be ineffective according to the accepted view (that pain is a phenomenon of the brain), but this has proven not to be the case and indeed, the rapid return to normal function with relief of pain in our patients suggests that no permanent central nervous system changes have occurred at all.

Our hypothesis also suggests a different organisation of pain mechanisms, which we believe may be supported by two classic neuroanatomic studies. The studies by Rexed (Rexed, "The cytoarchitectonic organization of the spinal cord in the cat", J Comp Neurol, 96 (1952), pp. 414-495) and Szentagothai (Szentagothai, "Neuronal and synaptic arrangement in the substantia gelatinosa rolandi", J Comp Neurol, 122 (1964), pp. 219-239) suggested at least some degree of separation between the peripheries and the brain at spinal cord level, a separation which probably formed the anatomic basis for spinal cord-mediated reflex functions such as withdrawal from a painful stimulus. We suggest that this points towards two levels of neurological function—spinal and supraspinal, the former with a largely reactionary/reflexive function and the latter coordinating multiple physiological, sensory and emotional responses to the painful stimulus.

The new pain channel hypothesis and embodiments of the treatment method described herein can lead to a change in focus in the diagnosis and management of pain and drive improvement in current technology and medications to facilitate effective treatment of persistent pain.

Those of skill in the art would understand that information and signals may be represented using any of a variety of technologies and techniques. For example, data, instructions, commands, information, signals, bits, symbols, and chips may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software or instructions, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. For a hardware implementation, processing may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. Software modules, also known as computer programs, computer codes, or instructions, may contain a number a number of source code or object code segments or instructions, and may reside in any computer readable medium such as a RAM memory, flash memory, ROM memory, EPROM memory, registers, hard disk, a removable disk, a CD-ROM, a DVD-ROM, a Blu-ray disc, or any other form of computer readable medium. In some aspects the computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media. In another aspect, the computer readable medium may be integral to the processor. The processor and the computer readable medium may reside in an ASIC or related device. The software codes may be stored in a memory unit and the processor may be configured to execute them. The memory unit may be implemented within the processor or external to the processor, in which case it can be communicatively coupled to the processor via various means as is known in the art.

Further, it should be appreciated that modules and/or other appropriate means for performing the methods and techniques described herein can be downloaded and/or otherwise obtained by computing device. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a computing device can obtain the various methods upon coupling or providing the storage means to the device.

Moreover, any other suitable technique for providing the methods and techniques described herein to a device can be utilized.

In one form the invention may comprise a computer program product for performing the method or operations presented herein. For example, such a computer program product may comprise a computer (or processor) readable medium having instructions stored (and/or encoded) thereon, the instructions being executable by one or more processors to perform the operations described herein. For certain aspects, the computer program product may include packaging material.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the disclosure is not restricted in its use to the particular application or applications described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope as set forth and defined by the following claims.

The invention claimed is:

1. A method for treating a patient in need of pain relief comprising:

selecting one or more nerves associated with a hypothesised source location of pain in a patient wherein each selected nerve is either within the hypothesised source location, in a sensory signal pathway upstream of the hypothesised source location, or in a sensory signal pathway bounding the hypothesised source location;

temporarily blocking each of the selected one or more nerves using a regional anaesthetic to identify one or more target nerves;

implanting in the patient, an electrode array of a neuromodulation apparatus in the skin or adjacent the hypodermis to overlie at least one of the one or more target nerves, and in use, the electrode array is stimulated by the neuromodulation apparatus to provide pain relief to the patient.

2. The method as claimed in claim 1 wherein the electrode array is implanted under the stratum corneum and in the dermis or hypodermis.

3. The method as claimed in claim 2 wherein the electrode array is implanted in the hypodermis.

4. The method as claimed in claim 3 wherein the electrode array is implanted adjacent the dermis in the hypodermis.

5. The method as claimed in claim 1 wherein the depth of the electrode array is selected to provide a stable field on the target nerve.

6. The method as claimed in claim 1 wherein each selected nerve is temporarily blocked for a time period sufficient to assess if blocking the nerve reduces the patient's pain below a predefined threshold level, and the target nerve is selected based on observed pain relief.

7. The method as claimed in claim 6, the time period is sufficient to assess if blocking the nerve eliminates the patient's pain.

8. The method as claimed in claim 6 wherein at least one selected nerve is blocked for a time period of at least 20 hours.

9. The method as claimed in claim 1, further comprising configuring the neuromodulation apparatus to provide a continuous conduction block to the respective target nerve.

10. The method as claimed in claim 9, wherein configuring the neuromodulation apparatus comprises:

selecting an initial pulse frequency, a pulse width, and an amplitude of a stimulation signal;

adjusting the amplitude to a level at which the patient just perceives the sensation.

11. The method as claimed in claim 10, further comprising further adjusting the pulse frequency and pulse width based on patient feedback.

12. The method as claimed in claim 10, wherein a template program stores the initial pulse frequency, pulse rate, and amplitude of a stimulation, and the method comprises selecting the template program on user interface of a controller, adjusting the initial settings, and then saving the settings in the neuromodulation apparatus.

13. The method as claimed in claim 1, further comprising determining the hypothesised source location of pain in the patient, through taking or reviewing a patient history, and performing a physical examination of the patient.

14. A method as claimed in claim 2, wherein the electrode array is implanted at a position near to a boundary between the dermis and hypodermis.

15. A method as claimed in claim 14, wherein each selected nerve is temporarily blocked for a time period sufficient to assess if blocking the nerve reduces the patient's pain below a predefined threshold level, and the target nerve is selected based on observed pain relief.

16. A method as claimed in claim 15 further comprising configuring the neuromodulation apparatus to provide a continuous conduction block to the respective target nerve.

\* \* \* \* \*